United States Patent [19]

Roberts et al.

[11] 4,430,887
[45] Feb. 14, 1984

[54] PIPE TESTER WITH MULTIPLE FLUID SOURCE CONNECTIONS

[75] Inventors: William M. Roberts, Deer Park; Fred L. Herman, Houston, both of Tex.

[73] Assignee: Hydra Systems Mfg, Inc., The Woodlands, Tex.

[21] Appl. No.: 358,244

[22] Filed: Mar. 15, 1982

[51] Int. Cl.³ .............................................. G01N 3/02
[52] U.S. Cl. ...................................... 73/49.5; 138/90; 141/327; 141/285
[58] Field of Search ...................... 73/40, 40.5 R, 49.1, 73/49.5, 49.6, 49.8; 138/90; 141/95, 285, 325, 326, 327

[56] References Cited

U.S. PATENT DOCUMENTS

| | | | |
|---|---|---|---|
| 2,497,193 | 2/1950 | Webb | 73/49.6 |
| 2,953,919 | 9/1960 | Potts | 73/49.5 |
| 3,064,467 | 11/1962 | Kortenhover | 73/49.6 |
| 3,095,929 | 7/1963 | McGuire et al. | 73/49.5 X |
| 3,331,238 | 7/1967 | Kost et al. | 73/49.5 |
| 3,695,641 | 10/1972 | Engelking et al. | 138/90 X |
| 3,844,313 | 10/1974 | Arnold | 138/90 |
| 4,192,177 | 3/1980 | Crickard et al. | 73/49.5 |
| 4,254,655 | 3/1981 | Keast et al. | 73/49.5 |

Primary Examiner—Gerald Goldberg
Assistant Examiner—Tom Noland
Attorney, Agent, or Firm—Vaden, Eickenroht, Thompson, Bednar & Jamison

[57] ABSTRACT

Apparatus is disclosed for hydrostatically testing a length of pipe wherein the pipe is adapted to be closed by plugs at each end, one of the plugs having a port to which a hose leading from a pump may be connected in order to fill the pipe with water, and the other plug having a bleed valve through which air may be vented from the pipe as it is filled. Pump pressure is applied to the water in order to test the pipe, and water is then drained from the pipe to permit the pump hose to be disconnected from one plug for use in testing another length of pipe.

11 Claims, 5 Drawing Figures

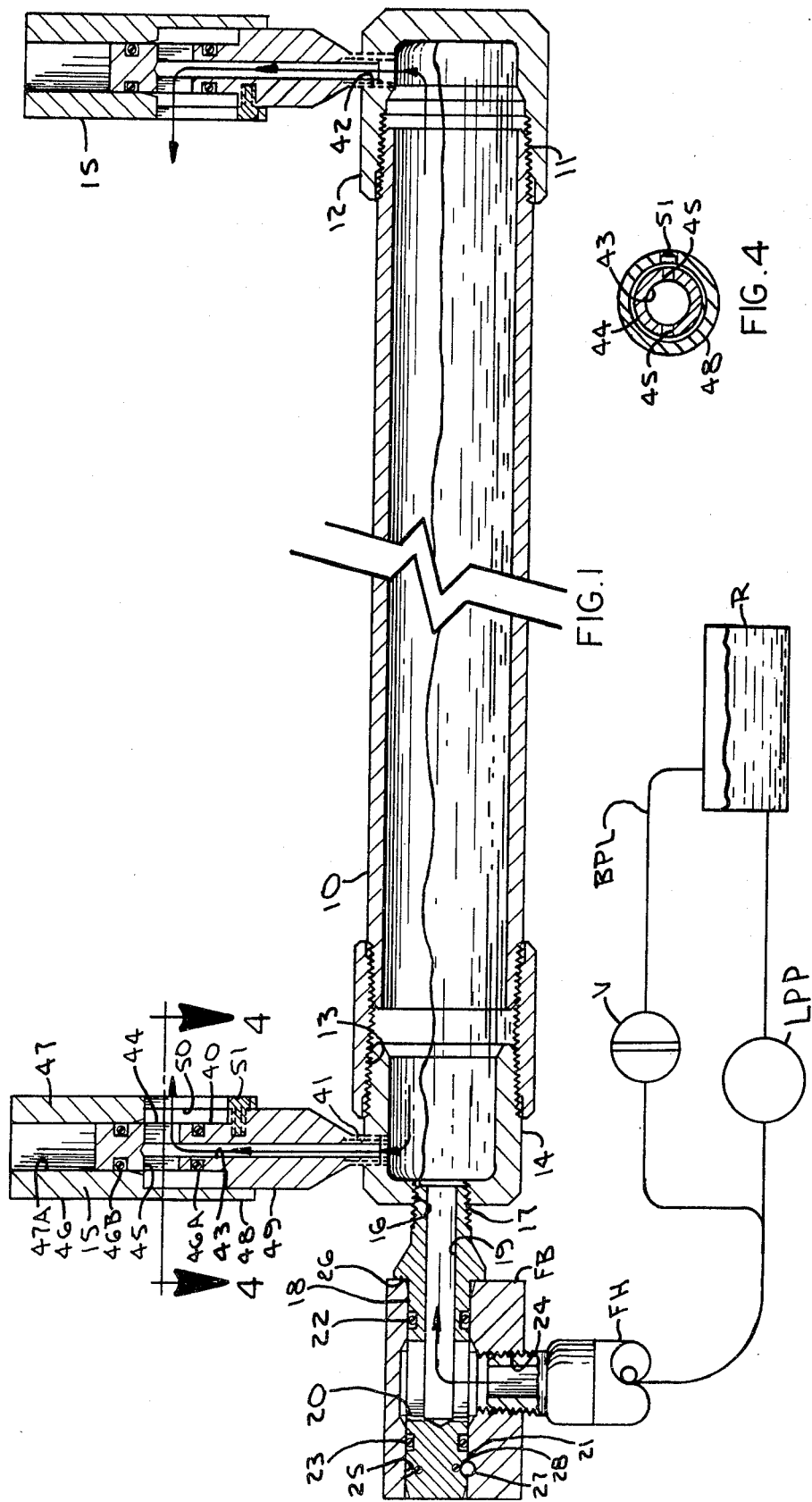

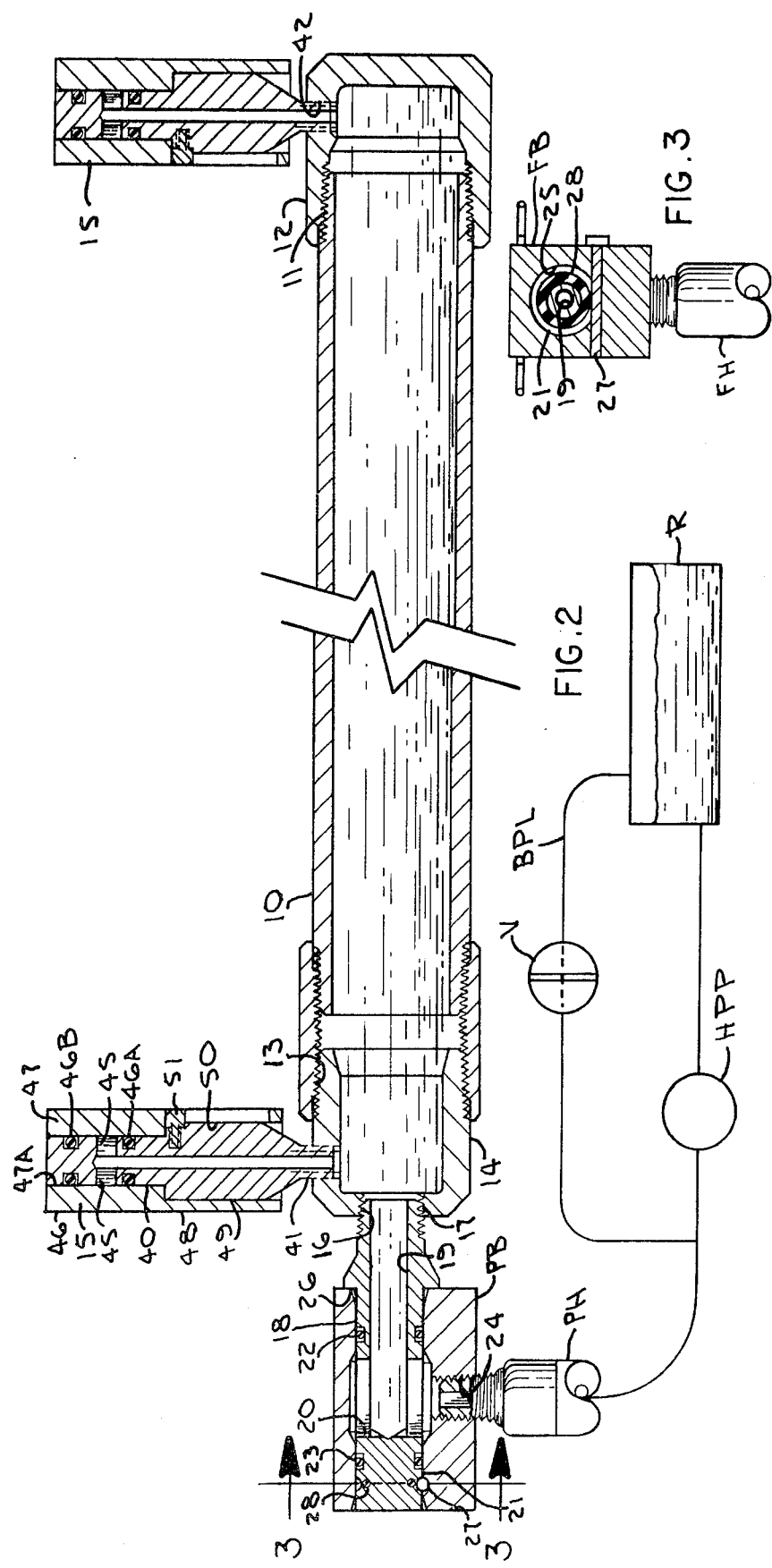

PIPE TESTER WITH MULTIPLE FLUID SOURCE CONNECTIONS

This invention relates to apparatus for use in hydrostatically testing a length of pipe. More particularly, it relates to improvements in apparatus of this type wherein the pipe is adapted to be closed by plugs at each end, one of which plugs has means to which a hose leading from a pump may be connected and the other of which plugs has a bleed valve which may be opened to vent air from the pipe, as it is filled, or closed to permit pump pressure to be applied to the water to test the pipe, following which the water may be drained from the pipe to permit the plug and hose connection to be used in testing another length of pipe.

It has been proposed to both fill the pipe and pressurize the water therein, when filled, by means of a single high pressure, low volume pump. This has the advantage of avoiding loss of water in that it does not require an interchange of pumps—i.e., the replacement of a low pressure, high volume pump for first filling the pipe with a low volume, high pressure pump for pressurizing the water which fills the pipe. On the other hand, this type of apparatus is inherently slow in operation due to the fact that the pipe is both filled and pressurized with a low volume pump.

Apparatus has also been proposed in which a single fitting or block adapted to be connected to the plug has connections for hoses from each of a high pressure, low volume and a low pressure, high volume pump. More particularly, a check valve in the fitting leading to the fill pump hose connection opens to permit the pipe to be filled, but closes as the high pressure pump is started in order to pressurize the water in the filled pipe. Although useful in the sense that it does not lose water, this apparatus ties up both the fill pump and the pressure pump, and is thus not practical, for example, in a production line wherein one pipe is being filled while a successive pipe, which has already been filled, is being pressurized. In addition, the fitting itself is of complex and expensive construction and may require frequent repair or replacement of the check valve therein.

In an effort to speed up the procedure, and avoid tying up both pumps in the testing of a single length of pipe, it has also been proposed to fill the pipe with water by means of a high volume pump, and then replace the high volume pump with a low volume, high pressure pump in order to replace water loss during the exchange of hoses and then pressurize the water. More particularly, it has been proposed to connect the interchangeable hoses and plug with a coupling which may be made up and broken up quicker than a standard threaded joint. For this purpose, a pin is threadedly connected to the end of the plug with a bore therethrough opening to the plug, and complementary parts of a hammer union are installed on the opposite ends of the pin and each hose to connect the hose with the bore of the pin and thus the plug. The pin enables the hoses to be connected to different plugs for closing the ends of various sizes of pipes.

An object of this invention is to provide apparatus of the latter type having connections for each of a high pressure and low pressure hose which can be made up and broken out in even less time and thus with less lose of water.

In a further effort to speed up the testing procedure, the bleed valve used with apparatus of this type is of such construction that it may be opened with a minimum of time and effort, particularly in comparison with the conventional needle valve. Thus, it comprises a body having a bore therein which is connectible to a hole in the plug, an outer cylindrical surface, and ports connecting the bore with the surface. A sleeve having a cylindrical bore is adapted to slide over the outer surface between an inner, closed position in which spaced-apart seal rings carried within the bore engage seal surfaces on opposite sides of the ports, and an outer, open position in which both seal rings and the inner end of the sleeve are on the outer side of the ports. Since the outer surface of the body and bore of the sleeve are cylindrical, water pressure does not create a force to move the sleeve out of either position to which it has been moved. However, although this valve is easily and quickly opened, the inner seal surface on the body is nevertheless left unprotected.

It is therefore still another object to provide a bleed valve for use with such apparatus which is not only quick opening, but also of such construction as to protect both the seal rings and the seal surfaces thereof in both positions, and further in which the seal rings may be easily and quickly replaced.

Difficulty may also be encountered in purging the pipe of air as it is filled with water. This is believed to occur because of the tendency of air to be trapped in the pipe at the end thereof near the fill hose, because of the turbulence created if the pumped fill water impinges on the plug at the other end of the pipe. It is therefore yet another object to provide such apparatus which enables the pipe to be more thoroughly purged, but without interfering with normal pipe filling procedures.

Still another object is to provide apparatus of the type above described in which each hose is connected to a single fitting or block which is of less complicated and less expensive construction than that above described, and which uses no internal parts which might require repair or replacement.

These and other objects, are accomplished in accordance with one embodiment of the present invention, by apparatus which includes a pin adapted to be connected to the plug and having an outer cylindrical surface, and a pair of spaced-apart seal rings carried about the surface on opposite sides of a port which connects a bore therein which opens to the plug when the pipe is connected to the plug. More particularly, the apparatus also includes a pair of blocks each having a cylindrical bore therein which is slidable over the cylindrical surface of the pin into a position in which seal surfaces within the bore on opposite sides of a threaded port connecting with its bore intermediate to the seal surfaces so as to connect the ports in the pin and block to one another.

The port in one such block is connectible to a hose from a low pressure, high volume pump, whereby the pipe may be filled with water while air is bled through the valve, and the port in the other block is connectible to a hose from a high pressure, low volume pump, whereby, upon removal and replacement of the one block with the other block, the water may be pressurized to test the pipe. Thus, as will be appreciated, each block is installed and removed merely by sliding its bore into and out of position over the cylindrical surface about the pin, thus resulting in considerable savings of time and considerably less loss of water. Furthermore, forces on the blocks due to water pressure are balanced in an axial direction so that it is unnecessary to latch or otherwise secure either block to the pin when positioned thereon.

In accordance with another embodiment of the present invention, the apparatus includes a pin of similar construction but having a longer outer cylindrical surface about which the seal rings are carried on opposite sides of a port connecting with the bore of the pin, and a single block having a cylindrical bore which is slidable longitudinally over the outer cylindrical surface of the pin. More particularly, the bore has three longitudinally spaced-apart seal surfaces, with the middle surface and one end seal surface being sealably engaged by the seal rings, in one longitudinal position of the block, and the middle surface and the other seal surface being sealably engaged by the seal rings in the other longitudinal position of the block. Thus, with the hose from a low pressure, high volume pump connected to a first port in the block intermediate the middle and one end seal surface, the pipe may be filled with water when the block is in its one position, and with a high pressure, low volume pump connected to a second port therein intermediate the middle and the other end seal surface, the water may be pressurized to test the pipe when the block is in the other position. As compared with the one block fitting previously described, there are no check valves or other parts which may require repair or replacement.

In accordance with another novel feature of the present invention, a bleed valve is connectable to the plug to which the pin is connected, as well as to the plug at the opposite end of the pipe, so that, like the bleed valve at the other end the bleed valve connected to the plug at its fill end may be opened until the pipe is filled to the level of its connection therewith, and then closed as the pipe continues to be filled.

In accordance with a still further novel feature of the present invention, each bleed valve preferably comprises a cap including a ring including body having a bore therein which opens to the plug, when the body is connected thereto, and an outer cylindrical surface having a pair of longitudinally spaced seal rings thereabout. More particularly, ports in the body connect its bore with the outer surface intermediate the seal rings, and a sleeve having a cylindrical bore is slidable over the outer surface of the body between an inner, closed position in which seal surfaces about the bore are sealably engaged with both seal rings, and an outer, open position in which the seal surfaces are outwardly of both seal rings. More particularly, the sleeve has a skirt on its inner end which is counterbored to form an annular space about the body surface, when the cap is in its open position, and a slot formed in the skirt is guidably slidable over a pin on the body to locate the slot opposite one of the ports and to prevent movement of the cap off of the end of the body.

In the drawings, wherein like reference characters are used throughout to designate like parts:

FIG. 1 is a longitudinal sectional view of apparatus constructed in accordance with the first described embodiment of the invention, including plugs closing both ends of a length of pipe and with the block for the fill hose installed on the outer end of the pin connected to one of the plugs in order to permit the pipe to be filled with water;

FIG. 2 is a longitudinal sectional view of the apparatus of FIG. 1, but upon replacement of the fill hose block with a block for the pressure hose in order to permit the water which fills the pipe to be pressurized, and showing bleed valves on each plug moved from the open positions of FIG. 1, during filling, to closed positions;

FIG. 3 is a cross-sectional view of the pin and one of the blocks, as seen along broken lines 3—3 of FIG. 2;

FIG. 4 is a cross-sectional view of one of the bleed valves as seen along broken lines 4—4 of FIG. 1.

Figure 5:
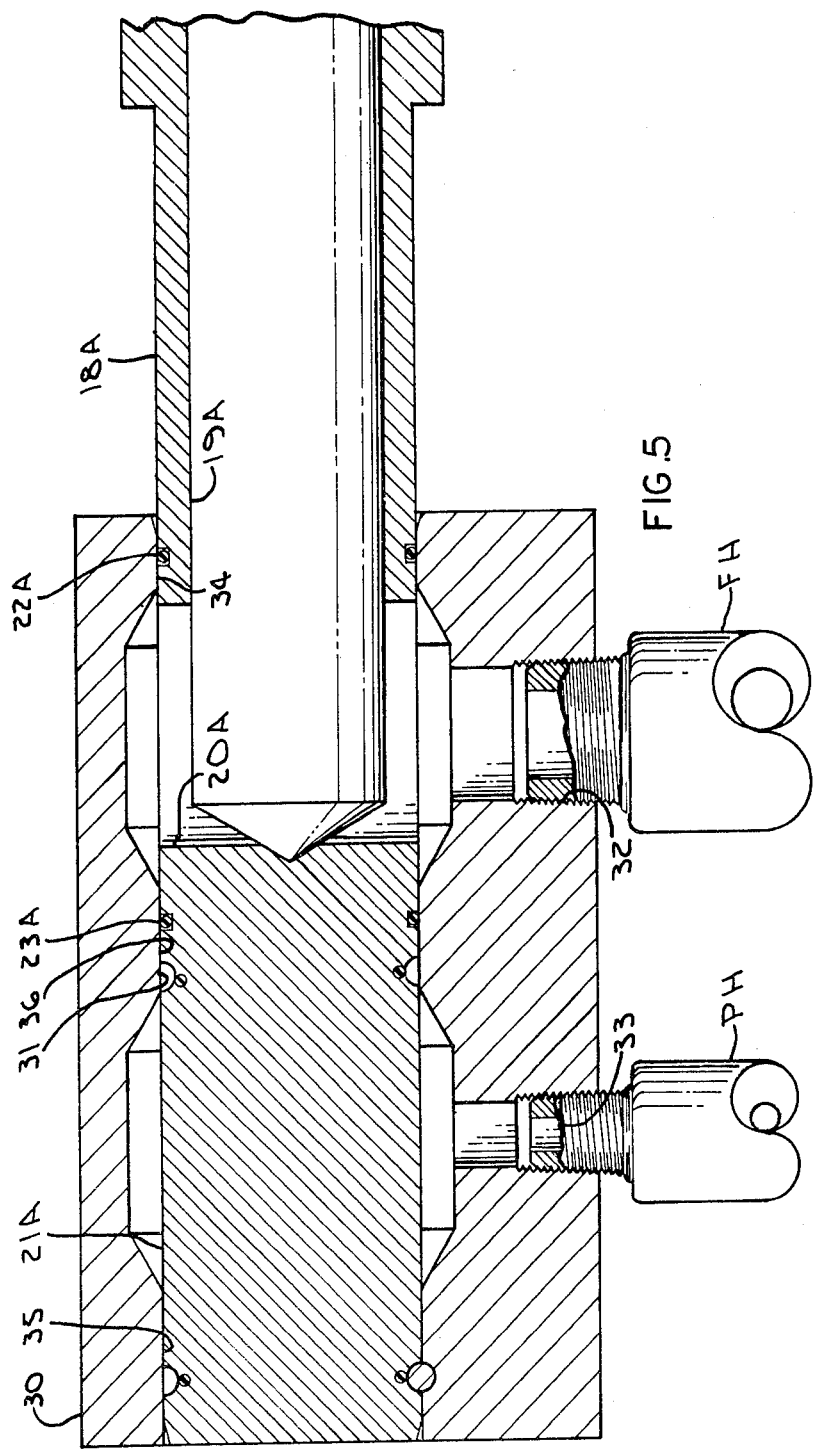
FIG. 5 is an enlarged cross-sectional view of the apparatus including a pin and single shiftable block constructed in accordance with an alternative embodiment of the invention, the block being shown shifted to its outer position on the pin during filling of the length of pipe.

The length of pipe 10 shown in each of FIGS. 1 and 2 has male threads 11 on its right hand end to which a plug 12 is connected and female threads 13 on a coupling on its left end to which a plug 14 is connected. As will be appreciated, the length of pipe may be a single joint or several threadedly connected joints. In any event, all of the threaded connections thereof are tested in accordance with the procedures to be described. As is common in the art, each plug 12 and 14 is of cup-shape, and, in accordance with one novel aspect of this invention, a bleed valve 15 is installed on not only the right plug 12 remote from the fill plug 14, but also the fill plug itself. As will be described, each such valve may be manually shifted between the open position of FIG. 1, in which air may be vented from the closed pipe, and the closed position of FIG. 2 to permit water which fills the pipe to be pressurized.

The outer end of the left hand plug 14 has a threaded hole 16 therein to which the inner threaded end 17 of a pin 18 is connected. The pin has a longitudinal bore 19 therein which opens to the plug at one end and which connects at its opposite end with ports 20 leading to a cylindrical surface 21 about the outer end of the pin. More particularly, seal rings 22 and 23 are carried within grooves about the cylindrical surface 21 on the inner and outer sides of the ports 20.

Each of the fill block FB shown in FIG. 1 and the pressure block PB shown in FIG. 2 is of the same construction, except for the size of a threaded port 24 therein which connects at its inner end with a bore 25 through the block which is adapted to slide over the outer cylindrical surface 21 of the pin. Thus, the port 24 of the fill block FB would ordinarily be of larger diameter than the port 24 of the pressure block PB in order to permit the larger fill hose FH to be connected thereto. In any event, the cylindrical bore 25 of each block fits closely over the outer cylindrical surface 21 of the pin, and has spaced-apart seal surfaces on its inner and outer ends for sealably engaging the inner and outer seal rings 22 and 23 when moved into position over the outer end of the pin. Thus, as shown, when so positioned the inner end of the block engages with shoulder 26 about the pin at the inner end of the outer cylindrical surface of the pin. When so located the block serves to connect either the fill hose FH or the pressure hose PH with the pin bore 19, and thus to fill the pipe 10 with water, pressurize the water, or permit the water to be drained from the pipe 10 back into the pump.

Inasmuch as the seal rings 22 and 23 are of the same effective sealing diameter, the forces on each block due to water pressure are balanced so that neither must be secured in its connecting position. To avoid accidental displacement, however, each block may be temporarily retained in such position by means of a small rod 27 removably inserted into a hole formed in the block tangent to its bore, and thus an annular groove about the outer surface 21 of the pin. As will be understood from FIGS. 1, 2 and 3, an O-ring 28 within the groove resists outward displacement of the pin due to its frictional engagement therewith.

As indicated diagramatically in FIG. 1, fill hose FH connects the fill block FB with a pump LPP which is of a low pressure, high volume type, and which receives water from a reservoir R located at the test site. The hydraulic system also includes a bypass line BPL which has a valve V installed therein. The valve V is of course closed as the pipe is filled, and the filled pipe pressurized, and then opened to permit water to drain from the pipe back into the reservoir.

As previously mentioned, each of the bleed valves 15 is opened as the pipe is filled, as shown in FIG. 1, and until fill water reaches the level of the connection of the valve with its plug. It may be desirable to fill the pipe as the pipe is inclined upwardly toward its right hand end, in which case the left hand bleed valve 15 would be closed, as shown in FIG. 2, prior to closing of the right hand valve. In any event, during the filling operation, the left hand bleed valve avoids trapping air which may otherwise accumulate in the left hand plug and left end of the pipe, especially when turbulence is caused in the area of the right hand plug due to impingement of the fill water on the inner side thereof.

When the pipe has been filled, the fill block FB is replaced with the pressure block PB, which, as shown in FIG. 2, is connected by pressure hose PH with pump HPP of a high pressure, low volume type. This pump may be connected in the same or a hydraulic system similar to that shown in FIG. 1 so as to receive water from a reservoir R. Thus, when the pump HPP is started, it initially makes up the small amount of water which may drain from the pin drain replacement of the blocks, and then pressurizes the water which fills the pipe to the desired level. During make up of fill water, the bleed valves may again be opened to permit air to be purged from the pipe, but they will of course be closed when the pipe is filled.

After the test has been completed, valve V may be moved from its closed to its open position, as indicated in broken lines in FIG. 2, so as to permit the water to drain from the pipe back through bypass line BPL into the reservoir R. When water has been drained from the pipe, the pressure block PB may be removed from the pin, and each of the plugs and thus the pin may be removed from the pipe length for installation on another length of pipe to be tested. As previously mentioned, the use of separate fill and pressure blocks enables the fill block to be installed on a pin connected to another pipe for the purpose of filling the other pipe as the already filled pipe is pressurized with the pressure block which has replaced the fill block.

As previously mentioned, and as shown in FIG. 5, pin 18A of the alternative embodiment of the present invention, is similar to the pin 18 of the first described embodiment insofar as its connection to the fill plug is concerned. Thus, it too has a bore 19A formed therein which opens to the plug 14 upon connection of the inner threaded end of the pin to the threaded hole in the plug. The pin 18A also has ports 20A formed therein which connect the outer end of bore 19A with an outer cylindrical surface 21A about the pin. Also, seal rings 22A and 23A are carried within grooves about the outer surface 21A on opposite sides of the port 20A.

As also previously described, in accordance with this embodiment of the apparatus, the pipe is filled with water, and the water then pressurized through connection of both a fill hose and pressure hose with a single block 30 which, similarly to each of the fill block FB and pressure block PB, has a bore 31 therethrough adapted to slide longitudinally over the cylindrical surface 21A of the pin. However, as compared with the fill and pressure blocks previously described, block 30 has two ports 32 and 33 connecting with the bore 31 therethrough, one such port 32 being threaded for connection with a relatively large diameter fill hose FH and the other port 33 being provided with a relatively small diameter thread for connection with a relatively large diameter pressure hose PH. These hoses of course extend for connection with low pressure, high volume and high pressure, low volume pumps installed within a hydraulic system as described in connection with FIGS. 1 and 2.

As shown in FIG. 5, the bore 31 of block 30 has seal surfaces 34 and 35 about its inner and outer ends as well as another seal surface 36 thereabout intermediate the seal surfaces 34 and 35. More particularly, each of the end seal surfaces is spaced from the intermediate seal surface a distance corresponding to the spacing between the seal rings 22A and 23A. Thus, the block 30 is longitudinally shiftable over the outer surface 18A of the pin between the outer position of FIG. 5, in which its seal surfaces 36 and 34 are sealably engaged with the seal rings 23A and 22A so as to connect the fill hose FH with bore 19A through the ports 20A during the fill operation, and an inner position (not shown), following filling, in which the right end of the block engages an outwardly facing shoulder about the pin to locate the seal surfaces 36 and 35 in sealing engagement with the seal rings 22A and 23A and thus connect the pressure hose PH with the bore 19A through the ports 20A. Thus, the pin and block cooperate to not only connect the desired hose with the pipe, but, at the same time, disconnect the other hose therefrom. More particularly, and as previously mentioned, this is done without the use of movable parts which may require replacement or repair.

As shown in FIGS. 1, 2 and 4, each bleed valve 15 comprises a body 40 having an inner threaded end 41 for connection with a threaded hole 42 in the side of the plug, and a bore 43 therein which extends through its inner end to the plug when the body is connected thereto. More particularly, each body has a cylindrical surface 44 about its outer end, and ports 45 therein which connect the bore 43 with the outer surface 44 intermediate inner and outer seal rings 46A and 46B, respectively, carried about the outer surface of the body. Each valve also comprises a cap including a sleeve 47 having a cylindrical bore 47A therein which fits closely over the outer cylindrical surface 44 of the body, and a skirt 48 on the inner end of the sleeve which is counterbored for fitting over an enlarged diameter portion 49 of the body intermediate its inner threaded end 41 and the outer cylindrical surface 44.

The cap is manually shiftable on the body between an outer position to open the valve, as shown in FIG. 1, and an inner position to close the valve, as shown in FIG. 2. In the closed position of the cap, seal surfaces on the bore 47A in the outer sleeve thereof are sealably engaged with the seal rings 46A and 46B to close off the ports 45. However, when the cap is shifted to its outer position, the inner sealing surface of the bore 47 is removed from about the seal ring 46A to connect ports 45 in the body with a longitudinal slot 50 formed in the skirt 48 through an annular space between the surface 44 about the body and the counterbore in the sleeve, whereby air is freely vented through the ports and out through the cap. More particularly, the slot 50 is located generally opposite one of the ports 45 by means of a screw 51 which is threaded to the enlarged diameter portion 49 of the body 40 for guidably sliding longitudinally within the slot as the cap is shifted between its inner closed position and its outer open position.

When the cap is shifted inwardly to its closed position, as shown in FIG. 2, the upper end of the slot engages the screw 51, and, when the cap is shifted outwardly to its open position, the inner end of the slot 50 will engage with the screw so as to prevent further outward movement of the cap. The screw 51 is of course removable to permit the sleeve to be removed from the outer surface of the body to permit access to the seal rings 46A and 46B for replacement or repair. At the same time, however, the skirt protects the seal rings against damage, not only when the cap is in its closed position, but also when it is in its open position.

From the foregoing it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

The invention having been described, what is claimed is:

1. Apparatus for use in hydrostatically testing a length of pipe, comprising a pair of plugs respectively connectible to opposite ends of the pipe to close same, a pin having means for connecting it to one of the plugs, a bore therein which opens to the one plug when the pin is connected thereto, an outer cylindrical surface having a pair of seal rings carried thereabout in spaced-apart relation, and ports connecting the bore with said outer surface intermediate the seal rings, a bleed valve for connection to the other plug to permit air to be bled from the pipe as it is filled, and a pair of blocks each having a bore therein slidable over the outer surface of the pin and into a position in which seal surfaces within its bore are sealably engaged by both seal rings, and a port therein connecting with its bore intermediate the seal surfaces, the port of one such block having means for connection to a hose from a low pressure, high volume pump, whereby the pipe may be filled with water while air is bled through the valve, and the port of the other block having means for connection to a hose from a high pressure, low volume pump, whereby, upon replacement of the one block and closing of the valve, the water may be pressurized to test the pipe.

2. Apparatus of the character defined in claim 1, wherein the pin has a shoulder thereabout engageable with a shoulder on each block to locate the block in said position.

3. Apparatus of the character defined in claim 2, including means for releasably retaining the block in said position.

4. Apparatus of the character defined in claim 1, including means for releasably retaining the block in said position.

5. Apparatus for use in hydrostatically testing a length of pipe whose opposite ends are respectively closed by a pair of plugs, one of which plugs has a threaded hole therein, and the other of which has a bleed valve thereon, said apparatus comprising a pin having a bore therein which opens to one end of the pin, and threads about such one end for connection with the threaded hole of the one plug, the pin also having an outer cylindrical surface and a pair of seal rings carried thereabout in spaced-apart relation, and ports connecting the bore with said outer surface intermediate the seal rings, and a pair of blocks each having a bore therein slidable over the outer surface of the pin and into a position in which seal surfaces within its bore are sealably engaged by both seal rings, and a port therein connecting with its bore intermediate the seal surfaces, the port of one such block being connectible to a hose from a low pressure, high volume pump, whereby the pipe may be filled with water as air is bled through the valve, and the port of the other block being connectible to a hose from a high pressure, low volume pump, whereby, upon replacement of the one block and closing of the valve, the water may be pressurized to test the pipe.

6. Apparatus of the character defined in claim 5, wherein the pin has a shoulder thereabout engageable with a shoulder on each block to locate the block in said position.

7. Apparatus of the character defined in claim 6, including means on the pin and bore of each block to releasably retain the block in said position.

8. Apparatus of the character defined in claim 5, including means releasably retaining the block in said position.

9. Apparatus for use in hydrostatically testing a length of pipe, whose opposite ends are respectively closed by a pair of plugs connected thereto, one plug having a threaded hole therein, and other plug having a bleed valve, said apparatus comprising a pin having a bore therein which opens to one end of the pin, and threads about such one end for connection with the threaded hole of the one plug, the pin also having an outer cylindrical surface and a pair of seal rings carried thereabout in spaced-apart relation, and ports connecting the bore with the outer cylindrical surface intermediate the seal rings, and a block having a cylindrical bore therein slidable longitudinally over the outer surface of the pin and into either of first and second alternate positions thereabout, and said block having three longitudinally spaced-apart seal surfaces within its bore, the middle surface and one end seal surface being sealably engaged by the seal rings, in the first position of the block, and the middle surface and the other end seal surface being sealably engaged thereby, in the second position of the block, said block also having a first port therein connecting with the bore intermediate the middle and one end seal surface, so that, with the block shifted to its first position and with a hose from a low pressure, high volume pump connected thereto, the pipe may be filled with water as air is bled through the bleed valve, and a second port therein connecting with the bore intermediate the middle and other end seal surface, so that, with the block shifted to its second position and with a hose from a high pressure, low volume pump connected thereto, the water may be pressurized to test the pipe when the bleed valve is closed.

10. In apparatus for use in hydrostatically testing a length of pipe, wherein a pair of plugs are respectively connected to opposite ends of the pipe to close same, a pin having a bore therein is threadedly connectible to a hole in one of the plugs with the bore opening to the plug, means are provided for releasably connecting a hose to the bore of the pin in order to fill the pipe with water, and then pressurize the water to test the pipe; the improvement comprising a valve for bleeding air from the pipe as it is filled, including a body having a bore therein, means for connecting the body to a plug with the bore opening to the plug, an outer cylindrical surface having a pair of longitudinally spaced seal rings carried thereabout, and ports connecting the bore with the outer surface intermediate the seal rings, and a cap including a sleeve having a cylindrical bore for sliding over the cylindrical surface of the body and a skirt on the inner end of the sleeve which is counterbored, said cap being longitudinally shiftable between an inner closed position in which the bore of the sleeve is sealably engaged by both seal rings and an outer open position in which the bore is removed from the inner seal ring and said skirt forms a cylindrical space about the outer surface of the body, said body having a pin which is guidably slidable longitudinally within the slot to locate it opposite one of the ports, in the open position of the cap, and prevent movement of the cap beyond each such position.

11. Apparatus of the character defined in claim 10, wherein the pin is screw threaded into the side of the body.

* * * * *